(12) United States Patent
Liou et al.

(10) Patent No.: US 12,161,290 B2
(45) Date of Patent: *Dec. 10, 2024

(54) SYSTEMS AND METHODS FOR HIGH-SPEED DATA TRANSMISSION ACROSS AN ELECTRICAL ISOLATION BARRIER

(71) Applicant: Intuitive Surgical Operations, Inc., Sunnyvale, CA (US)

(72) Inventors: Derek C. Liou, Cupertino, CA (US); John A Barton, San Jose, CA (US); Matthew M. McConnell, Scotts Valley, CA (US); Kierstin Gray Parrish, Boulder Creek, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/200,198

(22) Filed: May 22, 2023

(65) Prior Publication Data

US 2023/0292990 A1 Sep. 21, 2023

Related U.S. Application Data

(63) Continuation of application No. 17/052,125, filed as application No. PCT/US2019/035678 on Jun. 5, 2019, now Pat. No. 11,690,496.

(Continued)

(51) Int. Cl.
*A61B 1/00* (2006.01)
*A61B 1/05* (2006.01)
(Continued)

(52) U.S. Cl.
CPC ...... *A61B 1/00013* (2013.01); *A61B 1/00016* (2013.01); *A61B 1/051* (2013.01);
(Continued)

(58) Field of Classification Search
CPC ......... H01P 3/12; H04B 10/80; H04B 10/801; H04B 10/802; H05K 1/0243; H05K 2201/10098
See application file for complete search history.

(56) References Cited

U.S. PATENT DOCUMENTS

| | | |
|---|---|---|
| 6,133,808 A | 10/2000 | Arakawa |
| 11,690,496 B2 | 7/2023 | Liou et al. |

(Continued)

FOREIGN PATENT DOCUMENTS

| | | |
|---|---|---|
| CN | 103347455 A | 10/2013 |
| CN | 107550560 A | 1/2018 |

(Continued)

OTHER PUBLICATIONS

International Search Report and Written Opinion for Application No. PCT/US2019/035678, mailed on Sep. 26, 2019, 14 pages.

(Continued)

*Primary Examiner* — Aaron B Fairchild

(57) ABSTRACT

An illustrative system may include a radio frequency ("RF") transmitter electrically coupled to a first electrical circuit and electrically isolated from a second electrical circuit; an RF receiver having a top surface that is parallel with a top surface of the RF transmitter, the RF receiver electrically coupled to the second electrical circuit and electrically isolated from the first electrical circuit; and a waveguide between the RF transmitter and the RF receiver and configured to guide an RF signal representative of data between the RF transmitter and the RF receiver, the data provided by the first electrical circuit, the waveguide comprising an input port that at least partially covers the top surface of the RF transmitter, and an output port that at least partially covers the top surface of the RF receiver.

16 Claims, 6 Drawing Sheets

Related U.S. Application Data

(60) Provisional application No. 62/681,585, filed on Jun. 6, 2018.

(51) Int. Cl.
*A61B 1/313* (2006.01)
*H01P 3/12* (2006.01)
*H05K 1/02* (2006.01)
*A61B 1/045* (2006.01)

(52) U.S. Cl.
CPC ............. *A61B 1/313* (2013.01); *H01P 3/12* (2013.01); *H05K 1/0243* (2013.01); *A61B 1/045* (2013.01); *H05K 2201/10098* (2013.01)

(56) References Cited

U.S. PATENT DOCUMENTS

| | | | |
|---|---|---|---|
| 2008/0242342 A1* | 10/2008 | Rofougaran | H01P 1/20372 455/550.1 |
| 2012/0100729 A1 | 4/2012 | Edidin et al. | |
| 2013/0079680 A1 | 3/2013 | Stein et al. | |
| 2016/0261015 A1 | 9/2016 | Deriso | |
| 2018/0027647 A1 | 1/2018 | Rengarajan et al. | |
| 2021/0068617 A1 | 3/2021 | Liou et al. | |

FOREIGN PATENT DOCUMENTS

| | | |
|---|---|---|
| WO | WO-2013155193 A1 | 10/2013 |
| WO | WO-2017058620 A1 | 4/2017 |

OTHER PUBLICATIONS

International Preliminary Report on Patentability for Application No. PCT/2019/035678, mailed on Dec. 17, 2020, 08 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SYSTEMS AND METHODS FOR HIGH-SPEED DATA TRANSMISSION ACROSS AN ELECTRICAL ISOLATION BARRIER

RELATED APPLICATIONS

The present application is a continuation application of U.S. patent application Ser. No. 17/052,125, filed Oct. 30, 2020, which is a U.S. National Stage Application under 35 U.S.C. § 371 of International Application No. PCT/US2019/035678, filed on Jun. 5, 2019, which claims priority to U.S. Provisional Patent Application No. 62/681,585, filed on Jun. 6, 2018, each of which is hereby incorporated by reference in its entirety.

BACKGROUND INFORMATION

Electrosurgical energy is a safe and effective tool used during surgery. During an electrosurgical procedure, such as a minimally invasive surgical procedure that uses a computer-assisted surgical system, an electrosurgical unit located within an operating room generates and outputs high voltage, high frequency electrical current. The electrical current is applied to patient tissue by way of an active electrode to cauterize or otherwise manipulate the tissue. To safely return the electrical current from the patient back to the electrosurgical unit, a grounding pad is adhered to the patient's skin. Because the conductive surface area of the grounding pad is much larger than the active electrode, the electrical current is dispersed over a wide area, minimizing the heating of the tissue under the grounding pad and thereby preventing inadvertent patient burn.

To assist the surgeon during a typical electrosurgical procedure, an endoscope is used to provide images (e.g., stereoscopic video) of a surgical area that includes the tissue being cauterized. An exemplary endoscope includes a metal shaft that extends distally from a camera head into the patient. Circuitry at the distal end of the shaft captures images (either monoscopic or stereoscopic) using image sensors and transmits the images to circuitry in the camera head. The circuitry processes the images (e.g., by performing various control and data transmission functions on the images) and transmits data (e.g., video data) representative of the images to a display system located within the operating room by way of an electrical cable.

In some situations, the electrical cable inadvertently comes in contact with the floor of the operating room, a metal tray, or another grounded surface. In these situations, the electrical cable acts as a capacitor due to the gap that an outer insulative jacket of the electrical cable creates between wires included in the electrical cable and the ground surface. Because the electrical current applied by the active electrode is high frequency, the electrical current can pass through the capacitor formed by the electrical cable with relative ease. Hence, while the electrical cable is in contact with the grounded surface, a path to ground for the electrical current is created. For example, if the any portion of the metal shaft of the endoscope comes in contact with or in close proximity to patient tissue to which high frequency electrical current is being applied, the high frequency electrical current may, instead of being dissipated by the grounding pad, be capacitively coupled onto the metal shaft and travel through the circuitry included in the camera head to the grounded surface that the electrical cable is touching. As the high frequency electrical current is capacitively coupled onto the metal shaft, an electric discharge (e.g., an electric arc) may occur between the patient tissue and the metal shaft. Often, such a discharge causes no harm to the patient. But, capacitively coupled current creates a potential situation in which a discharge may injure (e.g., burn) a patient.

To prevent capacitive coupling of electrical current onto the metal shaft of the endoscope, the circuitry within the endoscope may include an isolation barrier that electrically isolates circuit components electrically and/or capacitively coupled to the shaft (or to components within the shaft) from circuit components connected to the wires included in the electrical cable. In this manner, an electrically conductive path between the metal shaft and the electrical cable is blocked.

While the isolation barrier may prevent capacitive coupling of electrical current onto the metal shaft of the endoscope, the isolation barrier disadvantageously presents a challenge for transmitting data between electrically isolated components, especially between electrically isolated components on a relatively small printed circuit board ("PCB") such as that used in a camera head of an endoscope. Conventional solutions for transmitting data across an isolation barrier implemented on similarly sized PCBs are limited in bandwidth and can only transmit data at relatively low data transmission rates (e.g., less than 1 gigabit per second ("Gbps")). But, these low data transmission rates may cause latency, poor image quality, and/or inefficiency in scenarios in which endoscopic images are presented to a surgeon in substantially real time, especially when the endoscopic images are data intensive (e.g., such as is the case with high-definition stereoscopic images).

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
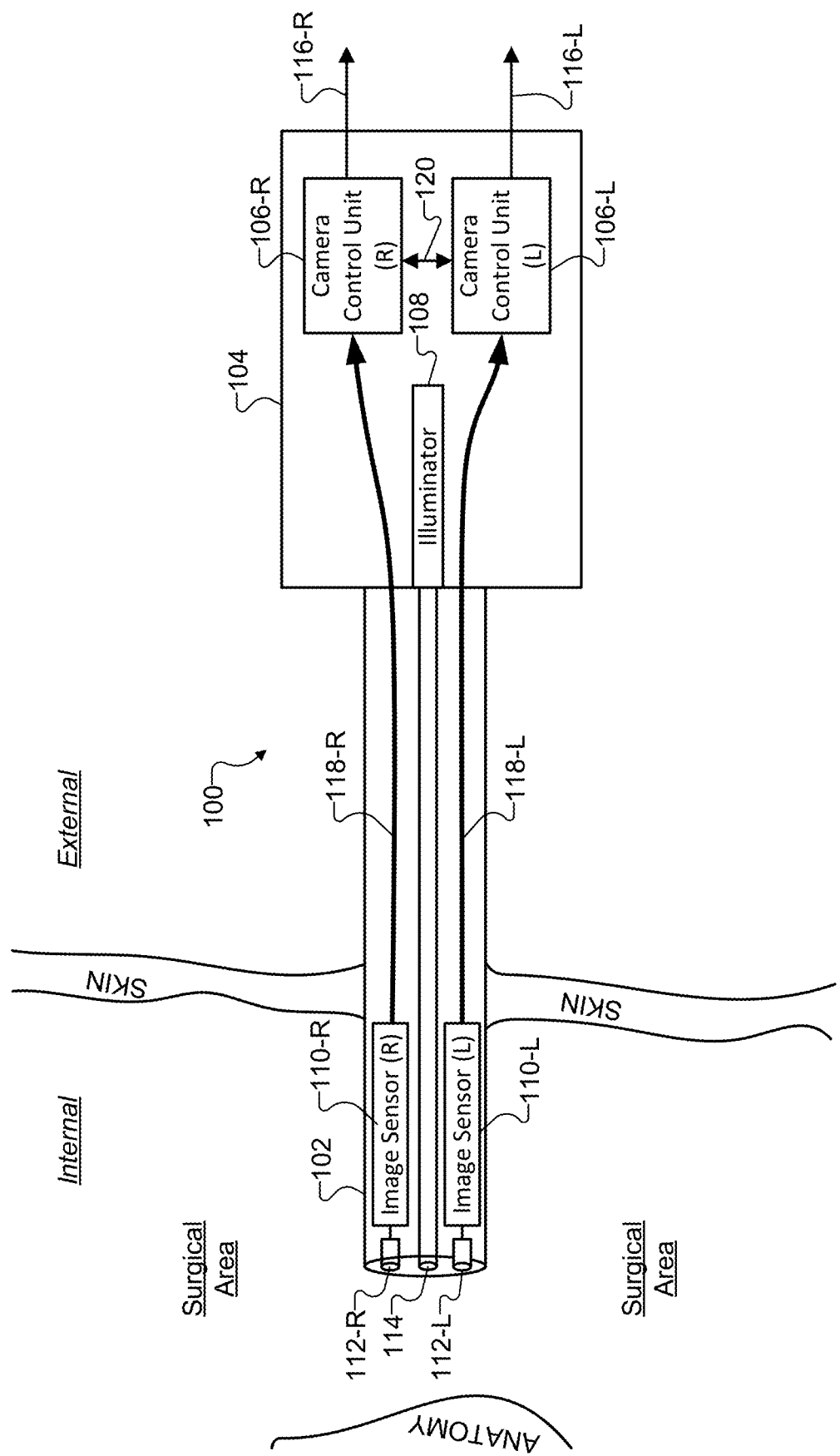
FIG. 1 illustrates an exemplary stereoscopic endoscope located according to principles described herein.

Systems and methods for high-speed data transmission across an electrical isolation barrier are described herein. As will be described in more detail below, an exemplary system may include a first electrical circuit, a second electrical circuit electrically isolated from the first electrical circuit, and a radio frequency ("RF") communication interface assembly all on a single PCB. The RF communication interface assembly is configured to allow high-speed transmission (greater than 1 Gbps) of data between the first and second electrical circuits. To this end, the RF communication interface assembly may include 1) an RF transmitter on the PCB, electrically coupled to the first electrical circuit, and electrically isolated from the second electrical circuit, 2) an RF receiver on the PCB out of direct RF signal path alignment with the RF transmitter, electrically coupled to the second electrical circuit, and electrically isolated from the first electrical circuit, and 3) a waveguide between the RF transmitter and the RF receiver and configured to guide an RF signal representative of the data between the RF transmitter and the RF receiver.

In some examples, the PCB is included in a surgical instrument configured to be used in a surgical procedure (e.g., a minimally invasive surgical procedure performed by a computer-assisted surgical system). To illustrate, the PCB may be housed within a camera head of an endoscope. In this illustration, a shaft (e.g., a conductive metal shaft) that includes one or more image sensors extends from the camera head. At the distal end of the shaft are one or more lenses or other optics configured to capture light reflecting from internal patient anatomy when positioned within a surgical area. The one or more image sensors convert the light to signals (e.g., digital data) representative of images and transmit the signals to the camera head by way of one or more conduits within the shaft. The first electrical circuit on the PCB processes the signals and generates data based on the signals. The data is representative of or is otherwise associated with one or more images of the surgical area. The first electrical circuit transmits the data across an electrical isolation barrier to the second electrical circuit by way of the RF communication interface assembly in any of the ways described herein. The second electrical circuit further processes the data and/or transmits the data via an electrical cable to a computing device located off of the PCB. For example, the second electrical circuit may transmit the data by way of the electrical cable to a computerized image processing device that is a part of a display system. The display system uses the data to display the one or more images.

Various benefits may be provided by the systems and methods described herein. For example, the systems and methods described herein allow high-speed transmission of data across an electrical isolation barrier implemented on a relatively small PCB, such as a PCB in a surgical instrument. In such configurations, the interface assembly used to allow the transmission of data across an electrical isolation barrier must be relatively small (e.g., implemented in a package that is approximately 30 mm by 16 mm by 8 mm). Conventional interface assemblies of this size (e.g., optoisolators) can only transmit data at relatively low data transmission rates (e.g., less than 1 Gbps). Other conventional interface assemblies (e.g., interface assemblies that include optical fibers and transceivers, RF communication interface assemblies that include a transmitter and a receiver within direct RF signal path alignment of each other, etc.) are too large to fit on PCBs in many surgical instruments and/or require multiple PCBs. For example, a conventional RF communication interface assembly includes an RF transmitter on a first PCB and an RF receiver on a second PCB positioned above the first PCB so that the RF transmitter and RF receiver are in direct RF signal path alignment (e.g., by having top surfaces of the RF transmitter and RF receiver face each other). However, such a conventional RF communication interface assembly may be too large to fit within a housing of a surgical instrument.

In contrast, the RF communication interface assemblies described herein may be implemented in relatively small packages (e.g., a package that is approximately 30 mm by 16 mm by 4 mm or of any other suitable size that allows the RF communication interface assemblies to be included on a PCB that is housed within a surgical instrument) while still allowing data transmission rates of greater than 1 Gbps (e.g., 2 Gbps or any other suitable data transmission rate greater than 1 Gbps). By allowing such high data transmission rates across an isolation barrier, the systems and methods described herein may enable efficient and real-time processing of data intensive content, such as high-definition stereoscopic images generated by a stereoscopic endoscope.

Furthermore, the RF communication interface assemblies described herein may be suitable for use in surgical settings, such as in an operating room. For example, the RF communication interface assemblies described herein are hermetically sealed and configured to withstand any suitable operating room sterilization process (e.g., an autoclave process, an ultrasonic cleaning, an alkaline chemical soak, etc.).

The systems and methods described herein reduce or eliminate the risk of electric discharge caused by capacitively coupled current onto a surgical instrument positioned within a surgical area. For example, by electrically isolating electrical circuits on a PCB located within a surgical instrument, and by using an RF communication interface assembly as described herein to transmit data between the electrical circuits, the systems and methods described herein prevent electrical current (e.g., high frequency current applied by an electrosurgical tool to patient tissue) from being capacitively coupled onto the surgical instrument and thereby creating an electric discharge that could potentially burn or otherwise harm the patient. This is especially the case when a surgical team inserts the surgical instrument into the patient through a non-electrically conductive (e.g., plastic) cannula instead of through an electrically conductive (e.g., metal) cannula that is, for example, connected to an electrical grounding pad.

The systems and methods described herein may operate as part of or in conjunction with manually controlled surgical instruments. For example, the systems and methods described herein may operate within a manually controlled endoscope.

Additionally or alternatively, the systems and methods described herein may operate as part of or in conjunction with a computer-assisted surgical system. A computer-assisted surgical system may use robotic and/or teleoperation technology to perform a surgical procedure on a patient. Exemplary computer-assisted surgical systems are described in U.S. Pat. No. 5,299,288 (filed Sep. 18, 1991)(disclosing "Image-directed robotic system for precise robotic surgery including redundant consistency checking"); U.S. Pat. No. 5,397,323 (filed Oct. 30, 1992)(disclosing "Remote Center-of-motion Robot for Surgery"); U.S. Pat. No. 5,402,801 (filed Apr. 28, 1994)(disclosing "System and Method for Augmentation of Surgery"); U.S. Pat. No. 5,417,210 (filed May 27, 1992)(disclosing "System and method for augmentation of endoscopic surgery"); U.S. Pat. No. 5,445,166 (filed Apr. 6, 1994)(disclosing "System for Advising a Surgeon"); U.S. Pat. No. 5,631,973 (filed May 5, 1994) (disclosing "Method for telemanipulation with telepresence"); U.S. Pat. No. 5,649,956 (filed Jun. 7, 1995)(disclosing "System and method for releasably holding a surgical instrument"); U.S. Pat. No. 5,696,837 (filed Apr. 20, 1995) (disclosing "Method and apparatus for transforming coordinate systems in a telemanipulation system"); U.S. Pat. No. 5,931,832 (filed Jul. 20, 1995)(disclosing "Methods for positioning a surgical instrument about a remote spherical center of rotation"); and U.S. Pat. No. 6,999,852 B1 (filed Oct. 26, 2004)(disclosing "Flexible robotic surgery system and method")—all incorporated herein by reference in their entirety. In addition, persons of skill in the art will be familiar with computer-assisted surgical systems such as the da Vinci Xi@Surgical System (Model IS4000) commercialized by Intuitive Surgical, Inc., Sunnyvale, California.

Various embodiments will now be described in more detail with reference to the figures. The systems and methods described herein may provide one or more of the benefits mentioned above and/or various additional and/or alternative benefits that will be made apparent herein.

FIG. 1 illustrates an exemplary stereoscopic endoscope 100. Endoscope 100 may be manually controlled (e.g., by a surgeon performing a surgical procedure on a patient). Alternatively, endoscope 100 may be coupled to a computer-assisted surgical system and controlled using robotic technology. Endoscope 100 is representative of many different types of endoscopes within which the systems and methods described herein may be used. For example, the systems and methods described herein may alternatively be used with a monoscopic endoscope.

As shown, endoscope 100 includes a shaft 102 and a camera head 104 coupled to a proximal end of shaft 102. Camera head 104 is configured to be located external to the patient. Shaft 102 has a distal end that is configured to be inserted into surgical area of a patient. As used herein, a "surgical area" of a patient may, in certain examples, be entirely within the patient and may include an area within the patient near where a surgical procedure is planned to be performed, is being performed, or has been performed. In other examples, a surgical area may be at least partially external to the patient. In various implementations, shaft 102 is rigid (as shown in FIG. 1). Alternatively, shaft 102 may be jointed and/or flexible.

As shown, camera head 104 houses a right-side camera control unit 106-R, a left-side camera control unit 106-L, and an illuminator 108. Shaft 102 houses a right-side image sensor 110-R optically coupled to a right-side optic 112-R, a left-side image sensor 110-L optically coupled to a left-side optic 112-L, and an illumination channel 114. The right-side components (i.e., camera control unit 106-R, image sensor 110-R, and optic 112-R) implement a camera that captures images 116-R of the surgical area from a right-side perspective. Likewise, the left-side components (i.e., camera control unit 106-L, image sensor 110-L, and optic 112-L) implement a camera that captures images 116-L of the surgical area from a left-side perspective.

To capture images 116, illuminator 108 generates light, which is carried by one or more optical fibers in illumination channel 114 and output into the surgical area at a distal end of shaft 102. Optics 112, which may each be implemented by a lens or other suitable component, capture the light after the light reflects from patient anatomy and/or other objects within the surgical area.

The light captured by optics 112 is sensed by image sensors 110. Image sensors 110 may be implemented as any suitable image sensors such as charge coupled device ("CCD") image sensors, complementary metal-oxide semiconductor ("CMOS") image sensors, or the like. Image sensors 110-R and 110-L convert the sensed light into signals (e.g., video data) representative of images, and transmit the signals to camera control units 106 by way of conduits 118-R and 118-L, respectively. Conduits 118 may be any suitable communication link configured to handle high-speed transmission of data.

Camera control units 106 process the signals received from image sensors 110 and generate, based on the signals, data representative of images 116. Camera control units 106 then transmit the data to an external device (e.g., a computing device that displays the images and/or video formed by the images on a display screen). As shown, camera control units 106 are synchronously coupled to one another by way of a communicative link 120 so that images 116 are synchronized.

Additional or alternative components may be included in endoscope 100. For example, one or more or other optics not explicitly shown in FIG. 1 may be included in shaft 102 for focusing, diffusing, or otherwise treating light generated and/or sensed by endoscope 100. In some alternative examples, image sensors 110 can be positioned closer to the proximal end of shaft 102 or inside camera head 104, a configuration commonly referred to as a rod lens endoscope.

The systems and methods described herein may be implemented within endoscope 100. For example, the systems and methods described herein may be used to transmit data between electrically isolated electrical circuits within endoscope 100 (e.g., within camera head 104) at a data transmission rate that is greater than 1 Gbps.

Figure 2:
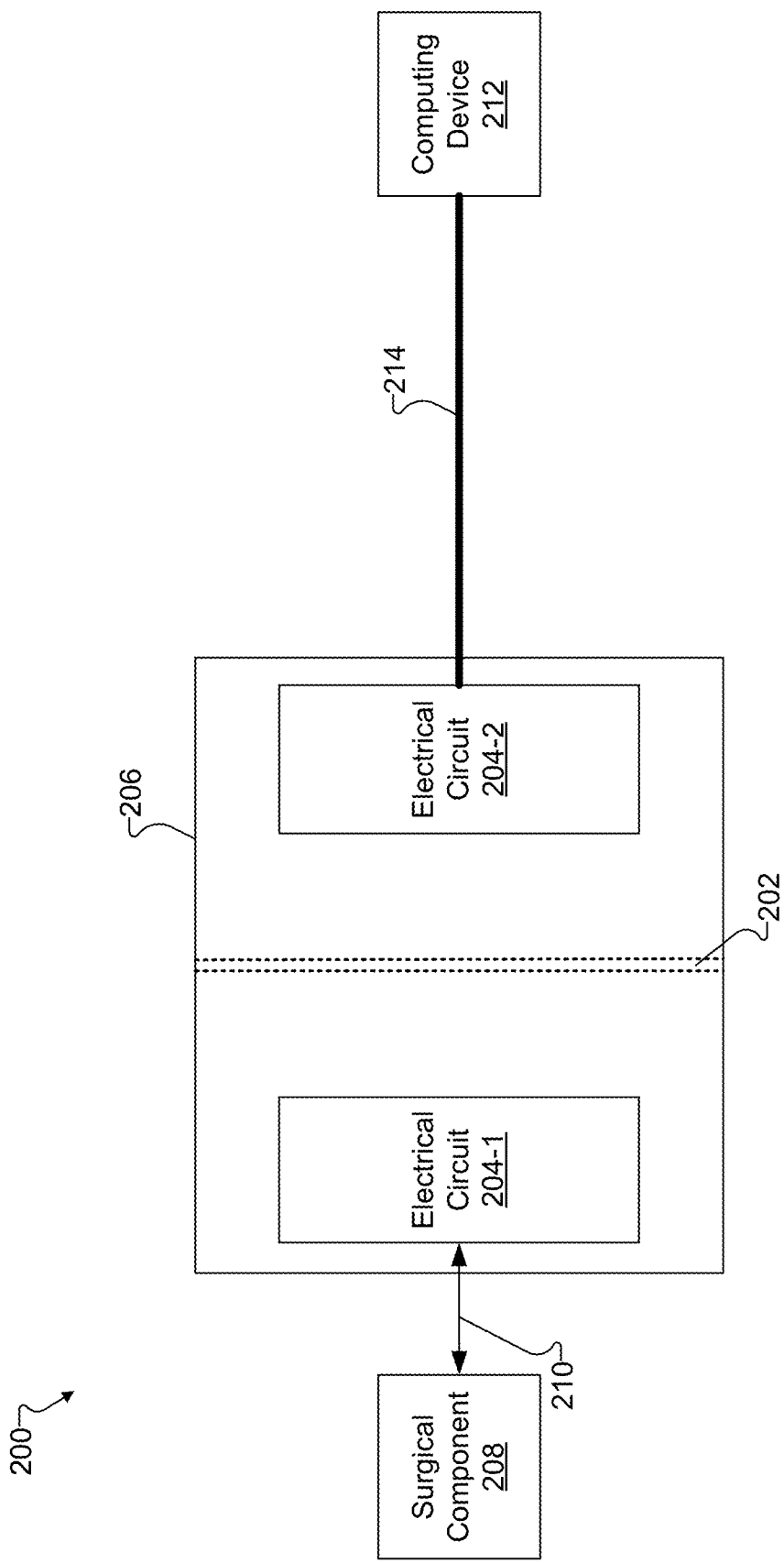
FIG. 2 illustrates an exemplary configuration in which an isolation barrier is used to electrically isolate a first electrical circuit on a PCB from a second electrical circuit on the PCB according to principles described herein.

FIG. 2 illustrates an exemplary configuration 200 in which an electrical isolation barrier 202 is used to electrically isolate a first electrical circuit 204-1 on a PCB 206 from a second electrical circuit 204-2 on PCB 206. As shown, first electrical circuit 204-1 is communicatively connected to a surgical component 208 by way of a connection 210, and second electrical circuit 204-2 is connected to a computing device 212 located off PCB 206 by way of an electrical cable 214. Each of these components will now be described.

PCB 206 is configured to mechanically support and electrically couple various electrical components included in electrical circuits 204-1 and 204-2 (collectively "electrical circuits 204"). For example, PCB 206 may include conductive pads to which electrical components may be soldered or otherwise electrically coupled, and conductive paths (e.g., traces, vias, etc.) that electrically interconnect the various electrical components. In some examples, non-conductive components (e.g., a housing of a free space optics interface assembly) may be attached (e.g., mechanically fastened, etc.) to PCB 206.

PCB 206 may be included within any suitable housing. For example, PCB 206 may be within a camera head (e.g., camera head 104) of an endoscope (e.g., endoscope 100). PCB 206 may alternatively be within any other type of surgical instrument and/or medical system component as may serve a particular implementation.

Electrical circuit 204-1 is configured to receive signals from surgical component 208 and generate or otherwise provide data based on the signals. The signals received from surgical component 208 may include data (e.g., video data) generated by image sensors 110 included in shaft 102. In other examples (e.g., when image sensors 110 are in camera housing 104), the signals received from surgical component 208 may be light signals provided by optics 112. Electrical circuit 204-1 may generate the data based on the signals in any suitable manner. For example, if the signals received from surgical component 208 include data generated by image sensors 110 included in shaft 102, electrical circuit 204-1 may generate data by processing the received data and generating new data based on the received data. In some alternative examples, electrical circuit 204-1 may simply receive and provide the data to electrical circuit 204-2 in its original format. If the signals received from surgical component 208 are light signals, electrical circuit 204-1 may generate the data by converting the light signals into data (e.g., video data) representative of images.

Electrical circuit 204-2 is configured to further process the data provided by electrical circuit 204-1 and/or transmit the data to computing device 212 by way of electrical cable 214. To this end, electrical circuits 204 may each include any number of passive or active electrical components (e.g., resistors, capacitors, integrated circuits ("ICs"), coils, etc.) interconnected in any suitable manner so as to perform one or more desired circuit operations. For example, electrical circuits 204 may include components that implement sensors 104, camera control units 112, and/or any other components included within camera head 104.

Electrical isolation barrier 202 electrically isolates electrical circuit 204-2 from electrical circuit 204-1. In other words, electrical isolation barrier 202 prevents any component included in electrical circuit 204-2 from being electrically connected in any way to any component included in electrical circuit 204-1. By so doing, electrical isolation barrier 202 prevents current (e.g., high frequency current applied to patient tissue by an electrosurgical tool) from being inadvertently capacitively coupled onto surgical component 208 when electrical cable 214 is in contact with a grounded surface (e.g., a floor of the operating room, a metal tray, etc.).

Electrical isolation barrier 202 may be implemented in any suitable manner. For example, electrical isolation barrier 202 may be implemented by PCB 206 including separate ground planes for each electrical circuit 204 (e.g., a first ground plane for electrical circuit 204-1 and a second ground plane separate and disconnected from the first ground plane for electrical circuit 204-2). Electrical isolation barrier 202 may be additionally or alternatively implemented in any other way (e.g., by maintaining a minimum physical distance between first and second electrical circuits 204, etc.).

Surgical component 208 may include any component configured to be positioned within a surgical area associated with a patient. In some examples, surgical component 208 may be a particular component of a surgical instrument used during a surgical procedure. For example, surgical component 208 may be implemented by a shaft (e.g., shaft 102) of an endoscope (e.g., endoscope 100). In some examples, surgical component 208 includes one or more conductive surfaces, such as an outer surface made out of a conductive metal, that may in some instances come in physical contact with patient tissue and/or patient fluid.

Surgical component 208 is connected to electrical circuit 204-1 by way of connection 210. Connection 210 may be implemented in any suitable manner. For example, one or more components within surgical component 208 may be electrically, optically, or otherwise coupled to electrical circuit 204-1. In this manner, electrical circuit 204-1 may receive signals from surgical component 208. To illustrate, if surgical component 208 is implemented by shaft 102 of endoscope 100, electrical circuit 204-1 may receive signals provided by one or more components in shaft 102. As another example, connection 210 may represent a capacitive coupling between surgical component 208 and electrical circuit 204-1. To illustrate, if surgical component 208 is a metal shaft of an endoscope, the metal shaft may be capacitively coupled to electrical circuit 204-1 by way of a capacitance that is created between the metal shaft and one or more conductive items (e.g., vias, traces, or components) included in electrical circuit 204-1.

Computing device 212 may include any suitable computing device located off PCB 206. For example, computing device 212 may be included in a computer-assisted surgical system, a display system, etc. Computing device 212 is configured to receive and process data transmitted from electrical circuit 204-2. For example, computing device 212 may display one or more images represented by the data on one or more display screens.

Electrical cable 214 includes one or more conductive wires configured to allow communication between second electrical circuit 204-2 and computing device 212. Electrical cable 214 further includes an insulative jacket that surrounds the one or more conductive wires. As mentioned, electrical cable 214 may come in contact with a grounded surface. When this happens, electrical cable 214 acts as a capacitor through which electrical current that has a sufficiently high frequency (e.g., greater than 100 kHz) can pass.

Figure 3:
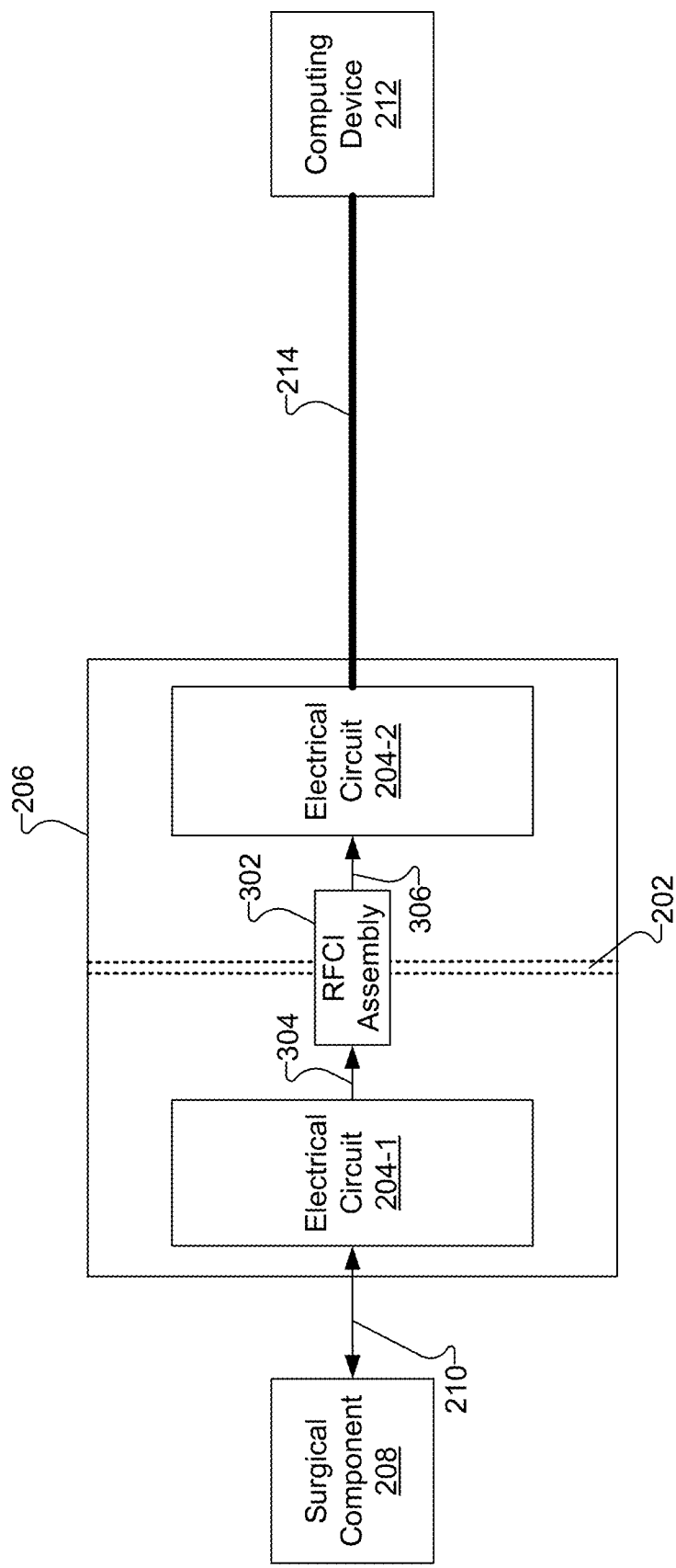
FIG. 3 illustrates an exemplary configuration in which a radio frequency communication interface assembly is on a PCB to allow transmission of data between electrically isolated electrical circuits according to principles described herein.

FIG. 3 shows an exemplary configuration in which an RF communication interface ("RFCI") assembly 302 is on PCB 206 to allow transmission of data between first electrical circuit 204-1 and second electrical circuit 204-2. As shown, RF communication interface assembly 302 includes an input 304 that is electrically connected to first electrical circuit 204-1 and an output 306 that is electrically connected to second electrical circuit 204-2. Various components that are included in RF communication interface assembly 302 will now be described.

Figure 4:
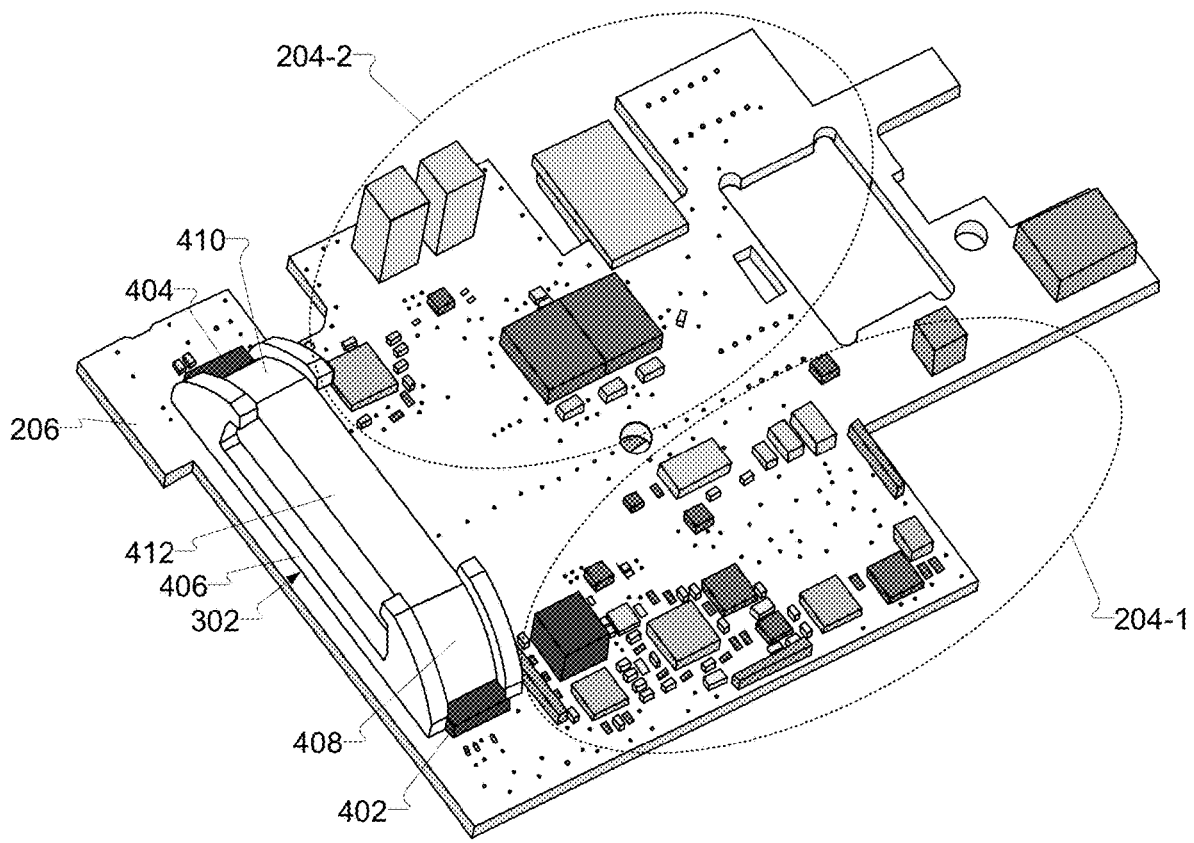
FIGS. 4-6 are various views of a radio frequency communication interface assembly configured to be on a PCB according to principles described herein.

FIG. 4 shows an exemplary perspective view in which RF communication interface assembly 302 is on PCB 206 together with various components included within first electrical circuit 204-1 and second electrical circuit 204-2. PCB 206 shown in FIG. 4 may be located, for example, within a surgical instrument (e.g., camera head 104 of stereoscopic endoscope 100). The components shown as being included in first and second electrical circuits 204-1 and 204-2 are merely illustrative of the many different types of components that may be on PCB 206 and included in first and second electrical circuits 204-1 and 204-2.

As shown, RF communication interface assembly 302 includes an RF transmitter 402, an RF receiver 404, and a waveguide 406. RF transmitter 402, RF receiver 404, and waveguide 406 are each attached to PCB 206 in any suitable manner. For example, RF transmitter 402 and RF receiver 404 may be electrically coupled (e.g., soldered) to conductive pads on PCB 206. Waveguide 406 may be mechanically fastened, adhered to, or otherwise connected to PCB 206 and/or to RF transmitter 402 and RF receiver 404.

RF transmitter 402 is electrically coupled to first electrical circuit 204-1. For example, RF transmitter 402 may be electrically coupled to one or more components within first electrical circuit 204-1 by way of one or more conductive paths (e.g., traces, vias, etc.) that are a part of PCB 206. RF transmitter 402 is electrically isolated from second electrical circuit 204-2. For example, isolation barrier 202 may electrically isolate RF transmitter 402 from second electrical circuit 204-2 in any of the ways described herein.

RF receiver 404 is electrically coupled to second electrical circuit 204-2. For example, RF receiver 404 may be electrically coupled to one or more components within second electrical circuit 204-2 by way of one or more conductive paths (e.g., traces, vias, etc.) that are a part of PCB 206. RF receiver 404 is electrically isolated from first electrical circuit 204-1. For example, isolation barrier 202 may electrically isolate RF receiver 404 from first electrical circuit 204-1 in any of the ways described herein.

RF transmitter 402 and RF receiver 404 may be implemented in any suitable manner. For example, RF transmitter 402 may be implemented by any suitable component configured to transmit an RF signal representative of data generated by first electrical circuitry 204-1. RF receiver 404 may be similarly implemented by any suitable component configured to receive an RF signal. To illustrate, in some examples, RF transmitter 402 is implemented by a transmitter IC configured to transmit RF signals and RF receiver 404 is implemented by a receiver IC configured to receive RF signals.

In some examples, the transmitter IC that implements RF transmitter 402 includes an IC configured to transmit RF signals in the extremely high frequency ("EHF") range (i.e., 30-300 gigahertz ("GHz")). Likewise, the receiver IC that implements RF receiver 404 includes an IC configured to receive RF signals transmitted in the EHF range. To illustrate, the transmitter IC and the receiver IC may be implemented by or similar to transmitter and receiver ICs manufactured by KEYSSA. However, such transmitter and receiver ICs are designed to transmit and receive data when in direct RF signal path alignment with each other. For example, the transmitter IC similar to transmitter ICs manufactured by KEYSSA is configured to emit RF signals in a direction that is perpendicular to a top surface of the transmitter IC, and a receiver IC similar to receiver ICs manufactured by KEYSSA is configured to receive RF signals in a direction that is perpendicular to a top surface of the receiver IC. Hence, the receiver IC must conventionally be positioned such that a top surface of the receiver IC is directly above and aligned with the top surface of the transmitter IC. In this configuration, the receiver IC may receive the RF signals transmitted by the transmitter IC.

However, as mentioned above, such a configuration is not possible in many surgical instruments due to size constraints of the surgical instruments. Moreover, regulatory requirements for distance and spacing between components on either side of an isolation barrier may prevent the transmitter and receiver ICs from being placed face-to-face in direct RF signal path alignment within a surgical instrument.

Hence, in accordance with the systems and methods described herein, RF transmitter 402 and RF receiver 404 are on the same PCB 206 and separated by a physical distance that is equal to or greater than a minimum spacing threshold (e.g., as defined by regulatory requirements) to achieve electrical isolation between first and second electrical circuits 204-1 and 204-2. In this configuration, RF transmitter 402 and RF receiver 404 have top surfaces that are parallel with PCB 206. RF transmitter 402 is configured to emit RF signals in a direction that is perpendicular to the top surface of RF transmitter 402, and RF receiver 404 is configured to receive RF signals in a direction that is perpendicular to the top surface of RF receiver 404. Because both RF transmitter 402 and RF receiver 404 are on PCB 206 with their respective top surfaces being parallel with PCB 206, RF transmitter 402 and RF receiver 404 are out of direct RF signal path alignment one with another.

As used herein, geometric terms, such as "parallel" and "perpendicular" are not intended to require absolute mathematical precision, unless the context indicates otherwise. Instead, such geometric terms allow for variations due to manufacturing or equivalent functions. For example, surfaces that are described as being "parallel" may not be exactly parallel, but may be parallel within a manufacturing tolerance range. Likewise, a direction that is "perpendicular" to a surface may not be exactly perpendicular to the surface, but may be perpendicular to the surface within a predetermined tolerance range.

As shown, waveguide 406 is between RF transmitter 402 and RF receiver 404. Waveguide 406 is configured to guide RF signals between RF transmitter 402 and RF receiver 404, which are out of direct RF signal path alignment one with another.

To illustrate, in some examples, RF transmitter 402 receives data from first electrical circuit 204-1. RF transmitter 402 modulates the data onto an RF signal and transmits the RF signal into waveguide 406. Waveguide 406 guides the RF signal across isolation barrier 202 towards RF receiver 404. RF receiver 404 detects the RF signal, demodulates the RF signal back into the data, and transmits the data to second electrical circuit 204-2.

To guide an RF signal from RF transmitter 402 to RF receiver 404, waveguide 406 includes a curved input segment 408 that includes an input port (not shown in FIG. 4) that at least partially cover the top surface of RF transmitter 402, a curved output segment 410 that includes an output port (not shown in FIG. 4) that at least partially cover the top surface of RF receiver 404, and a straight segment 412 in between and that connects curved input segment 408 to curved output segment 410. As will be described below, curved input segment 408, curved output segment 410, and straight segment 412 together define a chamber within waveguide 406 through which an RF signal may propagate from RF transmitter 402 to RF receiver 404.

Waveguide 406 may be made out of any suitable material. For example, waveguide 406 may be made out of a non-conductive material (e.g., a polyether ether ketone ("PEEK") material and/or a polyetherimide material, such as ULTEM®) configured withstand an operating room sterilization process.

Figure 5:
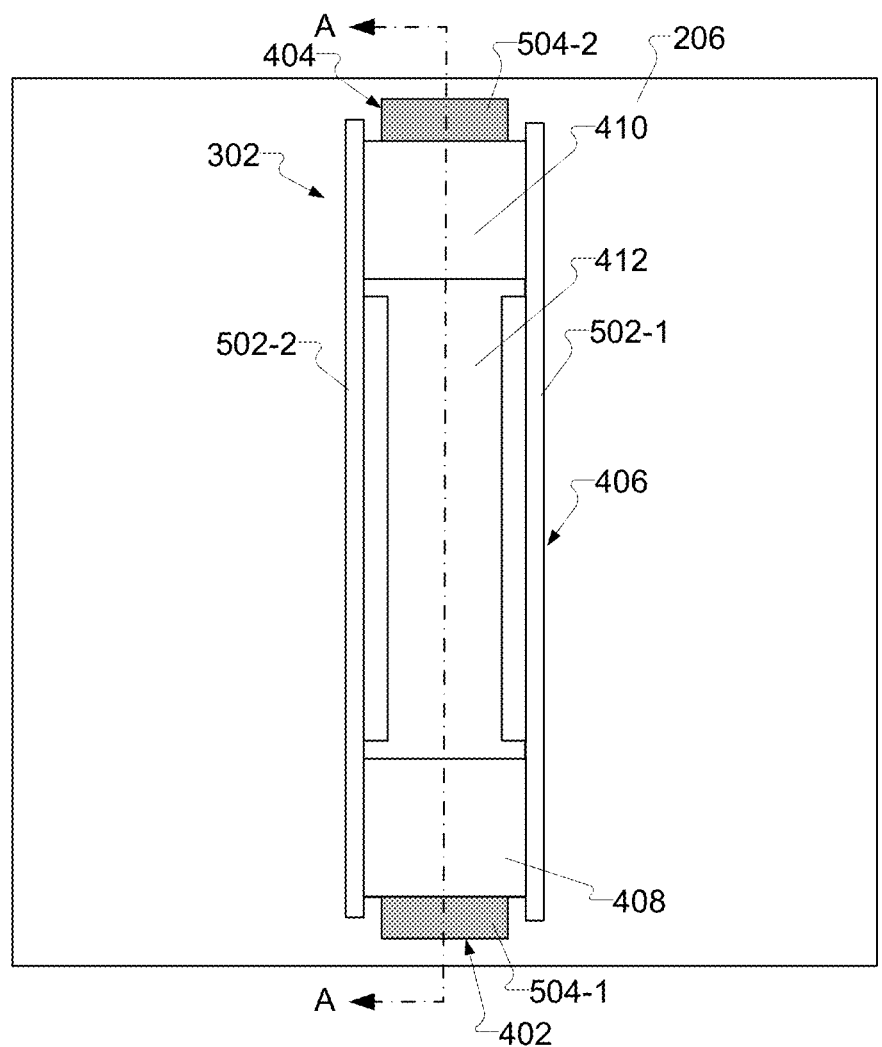
Figure 6:
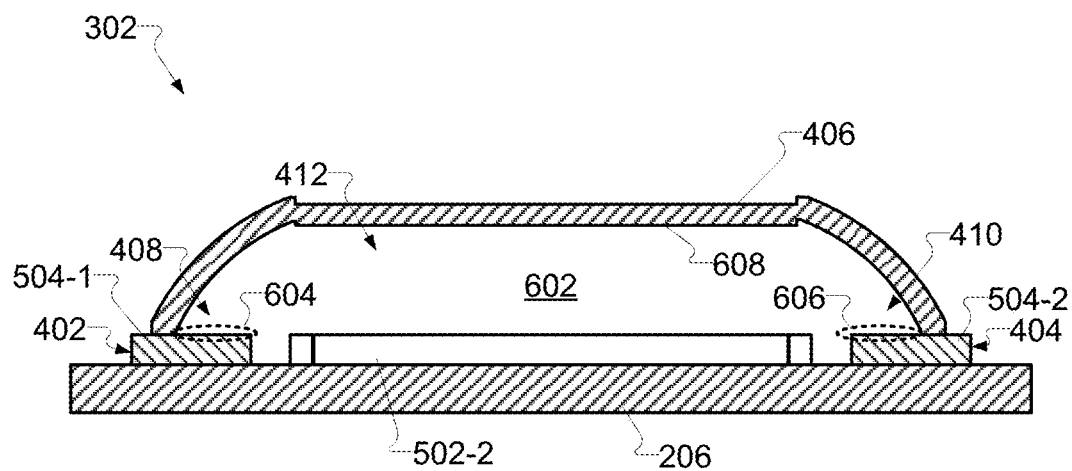

FIG. 5 illustrates a top view of RF communication interface assembly 302 on PCB 206. FIG. 6 illustrates a cross-sectional side view of RF communication interface assembly 302 taken along line A-A shown in FIG. 5. FIGS. 5-6 will be used to describe various features of RF communication interface assembly 302.

As shown in FIG. 5, waveguide 406 includes parallel flanges 502 (i.e., flanges 502-1 and 502-2) that run along a length of waveguide 406 and that are configured to be attached to PCB 206. Flanges 502 are attached to PCB 206 in any suitable manner. In some alternative embodiments, waveguide 406 does not include flanges 502, and is attached to PCB 206 in any other suitable manner.

FIGS. 5 and 6 both show that top surface 504-1 of RF transmitter 402 is partially covered by curved input segment 408 and that top surface 504-2 of RF receiver 404 is partially covered by curved output segment 410. In this configuration, as will be described in more detail with respect to FIG. 6, an RF signal generated by RF transmitter 402 may be guided by waveguide 406 to RF receiver 404.

As shown in FIG. 6, curved input segment 408, curved output segment 410, and straight segment 412 of waveguide 406 together define a chamber 602 (e.g., a hollow cavity) through which an RF signal propagates from RF transmitter 402 to RF receiver 404. The RF signal enters chamber 602 via an input port 604 included in curved input segment 408. Input port 604 may be implemented by any suitable port through which an RF signal may pass and enter chamber 602. As shown in FIG. 6, input port 604 partially covers top surface 504-1 of RF transmitter 402. In alternative embodiments, input port 604 completely covers top surface 504-1 of RF transmitter 402.

Curved input segment 408 guides the RF signal to travel initially in a perpendicular direction away from and with respect to top surface 504-1 of RF transmitter 402. The curvature of curved input segment 408 causes the RF signal to enter straight segment 412, where the RF signal travels in a parallel direction with respect to the top surface of PCB 206 and towards RF receiver 404. The RF signal then enters curved output segment 410, which causes the RF signal to travel in a perpendicular direction towards and with respect to top surface 504-2 of RF receiver 404. The RF signal exits waveguide 406 by way of an output port 606 included in curved output segment 410. RF receiver 404 then detects the RF signal. As shown in FIG. 6, output port 606 partially covers top surface 504-2 of RF receiver 404. However, in alternative embodiments, output port 606 completely covers top surface 504-2 of RF receiver 404.

In some examples, an inner surface 608 of waveguide 406 that surrounds chamber 602 is plated with a conductive material. The conductive material may include copper and/or any other material configured to aid in the propagation of RF signals through chamber 602. Additionally or alternatively, one or more outer surfaces of waveguide 406 are plated with a conductive material. For example, an outer surface of curved input segment 408 and curved output segment 410 may be plated with a conductive material, such as copper.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   a radio frequency ("RF") transmitter configured to be electrically coupled to a first electrical circuit and to be electrically isolated from a second electrical circuit;
   an RF receiver having a top surface that is parallel with a top surface of the RF transmitter, the RF receiver configured to be to be electrically coupled to the second electrical circuit and to be electrically isolated from the first electrical circuit; and
   a waveguide between the RF transmitter and the RF receiver and configured to guide an RF signal representative of data between the RF transmitter and the RF receiver, the data provided by the first electrical circuit, the waveguide comprising
   an input port that at least partially covers the top surface of the RF transmitter, and
   an output port that at least partially covers the top surface of the RF receiver.

2. The system of claim 1, wherein the RF transmitter is configured to emit RF signals in a direction that is perpendicular to the top surface of the RF transmitter.

3. The system of claim 1, wherein the RF receiver is configured to receive RF signals in a direction that is perpendicular to the top surface of the RF receiver.

4. The system of claim 1, wherein the waveguide is placed to guide the RF signals between the RF transmitter and the RF receiver by guiding the RF signals to travel initially in a perpendicular direction away from and with respect to the top surface of the RF transmitter, then in a parallel direction with respect to the top surface of the RF transmitter and towards the RF receiver, and then in a perpendicular direction towards and with respect to the top surface of the RF receiver.

5. The system of claim 1, wherein the waveguide comprises parallel flanges that run along a length of the waveguide.

6. The system of claim 1, wherein the waveguide is made out of at least one of a polyether ether ketone material or a polyetherimide material.

7. The system of claim 1, wherein:
   the waveguide comprises an inner surface that surrounds a chamber through which the RF signal travels from the RF transmitter to the RF receiver; and
   the inner surface is plated with a conductive material.

8. The system of claim 1, wherein the RF transmitter and the RF receiver are separated by a physical distance that is equal to or greater than a minimum spacing threshold required to achieve the electrical isolation between the first and second electrical circuits.

9. The system of claim 1, wherein:
   the RF transmitter is configured to
      receive the data from the first electrical circuit,
      modulate the data onto the RF signal, and
      transmit the RF signal into the waveguide; and
   the RF receiver is configured to
      detect the RF signal transmitted into the waveguide;
      demodulate the RF signal back into the data, and
      transmit the data to the second electrical circuit.

10. The system of claim 1, wherein the first electrical circuit is configured to transmit the data to the second electrical circuit by way of the RF transmitter, the RF receiver, and the waveguide at a data transmission rate of greater than 1 gigabit per second.

11. The system of claim 10, wherein the second electrical circuit is configured to transmit, by way of an electrical cable, the data to a computing device.

12. The system of claim 1, wherein the first electrical circuit and the second electrical circuit are on a printed circuit board ("PCB").

13. The system of claim 12, wherein the first electrical circuit is configured to:
   receive signals received from a surgical component configured to be positioned within a surgical area of a patient; and
   generate the data based on the signals.

14. The system of claim 13, wherein:
   the PCB is in a camera head of an endoscope; and
   the surgical component comprises a shaft that extends from the camera head and that comprises a distal end configured to be positioned within the surgical area.

15. The system of claim 13, wherein the electrical isolation of the second electrical circuit from the first electrical circuit prevents electrical current from being capacitively coupled onto the surgical component.

16. The system of claim 13, wherein the PCB comprises:
   a first ground plane for the first electrical circuit; and
   a second ground plane for the second electrical circuit, the second ground plane separate from the first ground plane;
   wherein the first and second ground planes electrically isolate the second electrical circuit from the first electrical circuit.

* * * * *